United States Patent [19]

Dunham

[11] 4,238,194

[45] Dec. 9, 1980

[54] NUCLEI ANALYSIS OF SOLID SUBSTANCES

[75] Inventor: Stuart B. Dunham, Schenectady, N.Y.

[73] Assignee: General Electric Company, Schenectady, N.Y.

[21] Appl. No.: 585,220

[22] Filed: Oct. 4, 1966

[51] Int. Cl.³ .......................................... G01N 31/00
[52] U.S. Cl. .............................. 23/230 R; 23/232 R; 73/28; 356/37
[58] Field of Search ..................... 73/28; 23/230, 232, 23/230 R, 232 R, 232 E; 356/37; 423/215.5

[56] References Cited

U.S. PATENT DOCUMENTS

| 2,656,256 | 10/1953 | Yeater ..................................... 23/230 |
| 2,684,008 | 7/1954 | Vonnegat ............................ 73/28 X |
| 2,897,059 | 7/1959 | Van Luik ............................ 23/232 E |
| 3,117,841 | 1/1964 | Van Luik, Jr. et al. ............... 23/232 |
| 3,198,721 | 8/1965 | Rich ........................................ 23/232 |
| 3,206,449 | 9/1965 | Van Luik, Jr. .......................... 73/28 |
| 3,410,662 | 11/1968 | Murphy .............................. 356/37 X |
| 3,410,663 | 11/1968 | Reilly et al. .................... 23/232 R X |
| 3,458,284 | 7/1969 | Rich et al. ......................... 356/37 X |
| 3,640,688 | 2/1972 | Walther .......................... 23/232 E X |

Primary Examiner—Richard E. Schafer
Attorney, Agent, or Firm—Leo I. MaLossi; James C. Davis, Jr.

[57] ABSTRACT

The presence of red phosphorus in solid form is detected through the use of a condensation nuclei detector and the preliminary steps of reacting the phosphorus body with ozone and then removing solid particles from a sample of the resulting gas mixture and forming phosphoric acid nuclei in the filtered gas sample.

4 Claims, 1 Drawing Figure

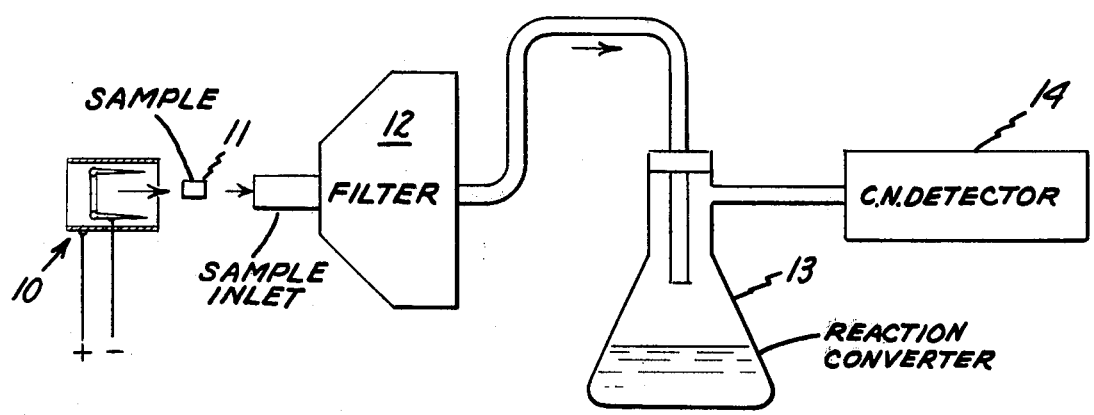

NUCLEI ANALYSIS OF SOLID SUBSTANCES

This invention relates to the condensation nuclei method of particle detection and more particularly to a method for detecting non-volatile substances having no sensible vapor pressure or dissociation temperature by the condensation nuclei technique.

Detection of gases and vapors in minute quantities is one of the outstanding properties of the condensation nuclei method of detection. In this method, a thorough description of which can be found in U.S. Pat. No. 3,117,841, VanLuik and Dunham, issued 1/14/64, the vapors or gases to be detected are converted to airborne particulates. The physical characteristics of the particulates are such that they will serve as the nucleus on which a fluid, such as water, will condense to form droplets. Such condensation nuclei comprise particles in a size range extending slightly above molecular size, or $1 \times 10^{-8}$ centimeter radius, to $1 \times 10^{-5}$ centimeter radius, although the most important radius sizes are those ranging from $5 \times 10^{-5}$ to $1 \times 10^{-7}$ cm.

The condensation nuclei method is well-suited for detecting those substances having high vapor pressures, that is comparatively volatile substances, since gases or vapors emanate from them quite naturally. Materials having higher vapor pressures have been rendered subject to condensation nuclei detection by a method known as thermoparticulate detection. A complete discussion of this process can be found in an article entitled "Condensation Nuclei, A New Technique for Gas Analysis", by F. W. VanLuik and R. E. Rippere, Analytical Chemistry, Vol. 34, Page 1617, November 1962, and to an article entitled "TPA—A New Method for Thermal Analysis of Polymeric Materials", by C. B. Murphy, F. W. VanLuik and A. C. Pitsas, appearing in Plastics Design and Processing Magazine, July, 1964. Generally, in the thermoparticulate approach, heat is applied to the substance to be detected and gases or vapors obtained by dissociation of the sample substance. Obviously if the material has no sensible dissociation temperature, thermoparticulate analysis cannot be used effectively.

It is a principal object of this invention to provide a process for detecting materials having no sensible vapor pressure or dissociation temperature by means of condensation nuclei processes.

It is another object of this invention to provide a process for detecting non-volatile substances by contacting the non-volatile with a gaseous material so that a portion of the non-volatile is chemically altered and gives rise to a vapor phase.

Other objects and advantages of this invention will be in part obvious and in part explained by reference to the accompanying specification and drawings.

In the drawings:

The FIGURE is a flow schematic illustrating how the method of this invention is effected.

Broadly, the method of this invention comprises contacting a non-volatile substance having no sensible vapor pressure or dissociation temperature with a gaseous material that is altered by its contact with the non-volatile substances. This altered material is then converted to condensation nuclei which are in turn received by a condensation nuclei detector.

As indicated above, one of the limitations of the condensation nuclei analysis techniques of detection is that many substances do not have a sensible vapor pressure or dissociation temperature so that there is no transport to the detector or to a suitable converter. Again, one method of inducing such emission is by controlled combustion such as done in the thermoparticulate analysis mentioned above. Since these procedures necessitate working directly with the material and since this is not always possible, the present process provides a novel and distinct method for obtaining a vapor or gas phase that can be handled by condensation nuclei detectors. More specifically, the present method utilizes the step of contacting the non-volatile sample substance with a gas which is chemically and/or compositionally altered by its contact with the sample. For example, chemical attack can be induced by introducing chemicals such as hydrochloric acid, nitric acid, ammonia, or ozone into the atmosphere surrounding the material to be detected. Under these conditions, the quantity of the chemical attack would, of course, be extremely limited but the airborne chemical still would be altered and a gaseous or vapor phase created as a result of the attack.

The process can also be effected by subjecting the non-volatile to radiant energy causing the surface to become activated and thereby result in induced emission. The material emitted goes into the gas passing over the non-volatile substance and is compositionally altered.

Discussing the process with particular reference to ozone as the reacting phase, the FIGURE of the drawings shows, schematically, an ozone generator 10 which, when energized, creates an electric wind induced by the corona and directs the ozone over the sample indicated by numeral 11. The ozone, being highly reactive, combines with part of the sample and is thereby altered. The product of the reaction is directed into the sample inlet through the filter 12 to remove any airborne contaminants and then into the converter 13 where the nuclei form droplets for subsequent detection by the condensation nuclei detector 14. As an example of materials which might be detected by the use of an ozonizer are red phosphorus from which phosphoric nuclei are produced and sulfur which is converted to sulfuric acid nuclei. The particular chemicals involved in the reaction converter would of course depend upon the chemistry of the materials to be detected.

It should be pointed out that an actual chemical reaction between the gas being passed over the sample and the samples itself is not necessary in all instances. For example, if the material to be detected can act as a surface catalyst for an airborne reaction, then actual chemical reaction is not necessary. An example would be the polymerization of an unsaturated hydrocarbon.

The present process provides, for the first time, a method utilizing a condensation nuclei detector on non-volatile substances having no sensible vapor pressure for dissociation temperature. This result is obtained by contacting the substance to be detected with a gaseous material that is chemically and/or compositionally altered by its contact with the non-volatile substance.

Although the present invention has been described in connection with preferred embodiments, it is to be understood that modifications and variations may be resorted to without departing from the spirit and scope of the invention, as those skilled in the art will readily understand. Such modifications and variations are considered to be within the purview and scope of the invention and the appended claims.

What I claim as new and desire to secure by Letters Patent of the United States is:

1. A method for detecting a non-volatile solid substance which comprises the steps of introducing into the atmosphere surrounding the said solid substance a reagent selected from the group consisting of nitric acid, hydrochloric acid, ammonia and ozone and chemically reacting the said solid substance in the atmosphere and thereby producing a gas reaction mixture containing a gaseous reaction product of the non-volatile solid substance, selecting a sample of the resulting gas mixture, filtering the gas mixture sample and removing substantially all non-gaseous material therefrom, converting the said gaseous reaction product to condensation nuclei, and detecting the resulting condensation nuclei with a condensation nuclei detector.

2. The process of claim 1 in which the non-volatile substance is red phosphorus and in which the gaseous reaction product is converted into phosphoric acid nuclei.

3. The process of claim 1 in which the non-volatile substance is sulfur and in which the gaseous reaction product is converted into sulfuric acid nuclei.

* * * * *